United States Patent
Kim et al.

(10) Patent No.: US 9,844,681 B2
(45) Date of Patent: Dec. 19, 2017

(54) BIOFEEDBACK APPARATUS USING MAGNETIC STIMULATOR AND CONTROL METHOD THEREFOR

(71) Applicant: MCUBETECHNOLOGY CO., LTD., Seoul (KR)

(72) Inventors: Jung Hoe Kim, Seoul (KR); Seung Tai Kim, Seoul (KR)

(73) Assignee: MCUBETECHNOLOGY CO., LTD., Seoul (KR)

( * ) Notice: Subject to any disclaimer, the term of this patent is extended or adjusted under 35 U.S.C. 154(b) by 267 days.

(21) Appl. No.: 14/652,603

(22) PCT Filed: Aug. 23, 2013

(86) PCT No.: PCT/KR2013/007581
§ 371 (c)(1),
(2) Date: Jun. 16, 2015

(87) PCT Pub. No.: WO2014/098347
PCT Pub. Date: Jun. 26, 2014

(65) Prior Publication Data
US 2015/0328475 A1 Nov. 19, 2015

(30) Foreign Application Priority Data
Dec. 18, 2012 (KR) .......................... 10-2012-0148364

(51) Int. Cl.
*A61B 5/00* (2006.01)
*A61N 2/00* (2006.01)
(Continued)

(52) U.S. Cl.
CPC .............. *A61N 2/004* (2013.01); *A61B 5/205* (2013.01); *A61B 5/227* (2013.01); *A61B 5/486* (2013.01);
(Continued)

(58) Field of Classification Search
CPC .......... A61B 5/22; A61B 5/224; A61B 5/227; A61B 5/202; A61B 5/205; A61B 5/207;
(Continued)

(56) References Cited

U.S. PATENT DOCUMENTS 5,853,005 A * 12/1998 Scanlon ................. A61B 5/113
29/235.5
5,984,879 A * 11/1999 Wallace ................. A61B 5/035
600/585
(Continued)

FOREIGN PATENT DOCUMENTS

CN 1423540 6/2003
CN 100358470 1/2008
(Continued)

OTHER PUBLICATIONS

International Search Report—PCT/KR2013/007581 dated Dec. 20, 2013.

*Primary Examiner* — Max Hindenburg
(74) *Attorney, Agent, or Firm* — Cantor Colburn LLP

(57) ABSTRACT

Provided is a biofeedback apparatus using a magnetic stimulator. In the biofeedback apparatus, a tube filled with a non-conductive fluid is disposed between a magnetic stimulator and patient's pelvic floor muscles to measure a change in pressure according to muscle exercise of the pelvic floor muscles, biofeedback is available without insertion of a tool for measurement of a pressure or an EMG (electromyogram) into vagina, urethra, or the like. In the biofeedback apparatus, since driving of the magnetic stimulator and driving of a pressure transducer do not influence each other, a controller can continuously monitor a state of change in pressure of the pelvic floor muscles by using the pressure transducer and, at the same time, can adjust a strength of a magnetic field generated from the magnetic stimulator to an optimal
(Continued)

strength according to the monitored state, so that it is possible to maximize the effect of treatment.

16 Claims, 6 Drawing Sheets

(51) Int. Cl.
    *A61B 5/22*     (2006.01)
    *A61B 5/20*     (2006.01)

(52) U.S. Cl.
    CPC .............. *A61B 5/6874* (2013.01); *A61N 2/00* (2013.01); *A61B 5/202* (2013.01)

(58) Field of Classification Search
    CPC ........ A61B 5/486; A61B 5/6874; A61N 2/00; A61N 2/004
    See application file for complete search history.

(56) References Cited

U.S. PATENT DOCUMENTS

| | | | | |
|---|---|---|---|---|
| 6,063,045 | A | * | 5/2000 | Wax .................. A61M 25/10 482/112 |
| 8,147,429 | B2 | * | 4/2012 | Mittal ................ A61B 5/04882 600/591 |
| 2004/0240121 | A1 | | 12/2004 | Etoh et al. |
| 2005/0240121 | A1 | | 10/2005 | Ferriss et al. |
| 2006/0047225 | A1 | | 3/2006 | Kang |
| 2012/0179063 | A1 | | 7/2012 | Bharucha et al. |

FOREIGN PATENT DOCUMENTS

| | | |
|---|---|---|
| CN | 101460218 | 6/2009 |
| CN | 102149426 | 8/2011 |
| DE | 102011014291 | 9/2012 |
| JP | 11146869 | 6/1999 |
| JP | 11333003 | 12/1999 |
| JP | 2006506167 | 2/2006 |
| KR | 100377104 | 3/2003 |
| KR | 1020060014743 | 2/2006 |
| KR | 100674042 | 1/2007 |
| KR | 1020070010671 | 1/2007 |
| KR | 1020070106964 | 11/2007 |
| KR | 100816847 | 3/2008 |
| KR | 1020110123831 | 11/2011 |

* cited by examiner

BIOFEEDBACK APPARATUS USING MAGNETIC STIMULATOR AND CONTROL METHOD THEREFOR

BACKGROUND OF THE INVENTION

1. Field of the Invention

The present invention relates to a biofeedback apparatus capable of simultaneously performing diagnosis and treatment of urinary incontinence or the like, and more particularly, to an effective biofeedback apparatus and a control method for the apparatus capable of simultaneously performing pressure measurement for diagnosis and magnetic stimulation for treatment by a configuration including a magnetic stimulator for treatment of urinary incontinence or the like and a pressure measurement device for biofeedback without insertion of a tool into a human body such as vagina or urethra.

2. Description of the Related Art

Treatment using biofeedback is a treatment method of measuring physiological phenomena occurring in a human body by using a sensor and helping a patient to adjust the physiological phenomena through patient's own exercise while monitoring the physiological phenomena visually or aurally.

Urinary incontinence is a symptom of leakage of urine which involuntarily occurs when an internal pressure of bladder exceeds a restraint force of urethral sphincter at the time of coughing or the like due to a failure of adjustment function of the bladder and the urethral sphincter muscles. Although the urinary incontinence occurs in both of women and men, the urinary incontinence manly occurs in women due to women's physical characteristics and parturition.

As treatment methods for the urinary incontinence, there are drug therapy, surgical treatment, and the like. However, since the methods have bad side effects, as more fundamental treatment methods, a treatment method using sphincter muscle strengthening exercise (Kegel exercise) or pelvic muscle strengthening exercise using biofeedback may be employed. The biological muscle exercise method using biofeedback is a complement of the Kegel exercise. In the biological muscle exercise method, the state of movement of the sphincter muscle is diagnosed by using an electromyogram (EMG) sensor or the like measuring the movement of the biological muscles. After monitoring the diagnosed state, the patient repeats a process of constricting the muscles and a process of adjusting a strength of a constriction force by adjusting patient's own muscles.

Through these processes, the sphincter muscle which is an involuntary muscle is strengthened in the exercise, so that the constricting pressure of the urethral sphincter muscle is increased. As a result, the effect of treatment improving the symptom of the urinary incontinence is obtained.

As described above, in addition to the biofeedback training where the patient does the muscle strengthening exercise with the patient's own force, there is developed a technique using a biological muscle stimulation method where muscle strengthening and biofeedback training can be performed by applying an electric stimulus to pelvic floor muscles to forcibly move weak muscles. As described later, various techniques for the biological muscles electric stimulation method was disclosed.

Korean Registered Patent No. 10-0377104 relates to a "body-cavity insertion electrode" and discloses an electrode which is inserted into an inner portion of vagina or anus to provide an EMG signal. FIG. 1 is a perspective diagram illustrating a body-cavity insertion electrode disclosed in the aforementioned patent.

Korean Registered Patent No. 10-0674042 relates to a "urinary incontinence treatment apparatus having a pressure sensor" instead of an EMG sensor as a method of performing biofeedback and electric stimulation and discloses a pressure sensor measuring a pressure and an electrode unit transmitting an electric stimulus to muscles inside a body cavity.

In addition, Korean Registered Patent No. 10-0816847 relates to a "urinary/anal incontinence treatment apparatus" and discloses a pressure sensor of measuring an internal pressure of a body cavity and an electrode unit of measuring a muscular strength of an anal sphincter muscle or pelvic floor muscles or applying an electric stimulus.

The apparatus disclosed in the above patent is a treatment apparatus using electric stimulation including an electrode which is inserted into the body cavity to be in direct contact with the muscle to applying the electric stimulus.

In the apparatus, since the electrode having an electric conductivity is exposed to an outside, there is a problem in that the electrode is not easy to perform cleaning, sterilization, and disinfection. As a result, the repetitive use of the unclean apparatus may result in infection in the patient. In addition, since the apparatus is inserted into the body, there is a problem in that the use is inconvenient and the patient feels discomfort. In addition, since the apparatus directly applies an electric stimulus to a human body, there is problem in that, sometimes, the patient suffers from an electrical burn injury or feels pain.

The apparatus of the related art which performs the biofeedback using the EMG signal and the electric stimulation performs an EMG measurement function of allowing a patient to move pelvic muscles with patient's own will and monitor the movement state and an electric stimulation function of forcibly applying an electric stimulus to patient's sphincter muscle to forcibly move the sphincter muscle. In the apparatus of the related art, in general, since the same electrode is used for performing the EMG measurement function and the electric stimulation function, there is a problem in that the EMG measurement causing the biofeedback and the electric stimulation causing forcible movement cannot be simultaneously performed. Namely, the EMG measurement and the EMG stimulation (or electric stimulation) are only to be sequentially performed. In this manner, in the case where the measurement and the stimulation are sequentially performed, since the patient cannot immediately compare the strength of the movement of the sphincter muscle caused by the patient's own force and the strength of the movement of the sphincter muscle caused by the force of the electric stimulation, the evaluation of the treatment course and the state of the muscles is unclear. Therefore, in the case where long-term repetitive treatment is required, the patient may give up the treatment on the way. Since the biofeedback apparatus of the related art cannot simultaneously perform the measurement and the stimulation, there is a problem in that the efficiency is deteriorated.

On the other hand, in order to solve the problem of the aforementioned insertion type electric stimulation treatment method such as infection, discomfort, skin damage, or the like, a urinary incontinence treatment apparatus using a magnetic field was developed. The urinary incontinence treatment apparatus using the magnetic field is a non-contact, non-insertion type treatment apparatus and has an advantage of solving problems associated with infection and the problem of discomfort at the time of use. However, in the case of applying the biofeedback at the time of the magnetic stimulation treatment, there is a problem in that it is not easy to detect an internal pressure of a body cavity or an EMG signal. In the method, a magnetic stimulator applies a high voltage to a stimulation coil to generate a strong pulsed magnetic field having a strength of several tesla and applies the pulsed magnetic field to a human body. Since a pressure sensor or an EMG sensor configured with semiconductors and wire lines is influenced by the strong pulsed magnetic field, there is a problem in that the pressure sensor or the EMG sensor is not easy to use together with the magnetic stimulator.

In this manner, although the magnetic stimulator used for the urinary incontinence treatment or the like has many advantages in comparison with other electric stimulation apparatuses, the biofeedback using the EMG sensor or the pressure sensor using the electrode which is to be influenced by the magnetic field is not available.

In addition, in the related art, in order to measure the internal pressure or the EMG signal of the body cavity such as vagina or urethra, a measurement tool is inserted into the human body, so that there is a problem in that the patient feels discomfort or pain. Due to these problems, a technique of measuring the pressure of the body cavity such as vagina or urethra without insertion of a tool into the human body is required.

SUMMARY OF THE INVENTION

The invention is to provide a biofeedback apparatus capable of measuring a signal for biofeedback without insertion of a separate tool into a body cavity such as vagina or urethra.

The invention is to provide a biofeedback apparatus capable of effectively treating urinary incontinence by detecting a biofeedback signal without insertion of a tool into a human body and simultaneously or cooperatively performing detection of the biofeedback signal and magnetic stimulation for strengthening muscles.

According to a first aspect of the invention, there is provided a biofeedback apparatus including: a pressure transducer which senses a pressure applied from an outside by using a fluid and supplies a pressure signal; a controller which generates a biofeedback signal by using the pressure signal supplied from the pressure transducer and outputs the biofeedback signal; and a display unit which outputs the biofeedback signal supplied from the controller on a screen, wherein the pressure transducer includes: a tube which is configured with a soft material of which shape is variable according to an external pressure and is filled with the fluid; a pressure sensor which senses the pressure applied to the tube to output a pressure signal; and a pressure transfer member which is disposed between the tube and the pressure sensor to transfer the pressure of the tube to the pressure sensor.

In the above biofeedback apparatus according to the first aspect, preferably, the fluid is configured with a flowable material which is non-conductive or non-magnetic so as not to be influenced by a magnetic field or an electromagnetic field. As an example, a flowable liquid, gel, gas, or the like may be used.

In the above biofeedback apparatus according to the first aspect, preferably, the controller includes: a biofeedback signal output module which receives the pressure signal from the pressure transducer, detects a value of difference between the received pressure signal and a pre-defined reference pressure value, and outputs the value of difference as the biofeedback signal; a reference point setting module which receives the pressure signal from the pressure transducer and sets a reference pressure value by using the received pressure signal according to a reference pressure value setting request input from an outside; a fluid injection control module wherein, in the case where the pressure signal supplied from the pressure transducer deviates from a pre-defined allowable range, the fluid injection control module determines a fluid amount to be injected into the tube or discharged from the tube according to a degree of deviation from the allowable range and generates a fluid injection driving signal according to a value of difference between the determined fluid amount and a current fluid amount to supply the fluid injection driving signal to the fluid injector; and a magnetic stimulator control module which receives the biofeedback signal from the pressure transducer, determines a strength of the magnetic field corresponding to the biofeedback signal, and generates the stimulator driving signal for driving the magnetic stimulator according to the determined magnetic field to supply the stimulator driving signal to the magnetic stimulator.

In the above biofeedback apparatus according to the first aspect, preferably, the connection pipe is a configured with a rigid material of which shape is not variable according to an external pressure.

In the above biofeedback apparatus according to the first aspect, preferably, the biofeedback apparatus further includes a fluid inlet which is formed in the tube or the connection pipe, and the internal pressure of the tube is adjusted by further injecting or discharging the fluid through the fluid inlet, and preferably, the tube further includes an air outlet, and air of an inner portion of the tube is discharged to an outside through the air outlet.

In the above biofeedback apparatus according to the first aspect, preferably, the pressure transducer further includes a fluid injector connected to the fluid inlet, and the fluid injector injects the fluid into the tube or discharges the fluid from the tube through the fluid inlet.

In the above biofeedback apparatus according to the first aspect, preferably, the biofeedback apparatus further includes a magnetic stimulator which generates and emits a magnetic field according to a stimulator driving signal, the tube of the pressure transducer is disposed at a position which is influenced by the magnetic field of the magnetic stimulator, and the pressure sensor is disposed at a position which is not influenced by the magnetic field of the magnetic stimulator.

In the above biofeedback apparatus according to the first aspect, preferably, the biofeedback apparatus is used for urinary incontinence treatment, and the magnetic stimulator is formed to have a shape of a chair so that a magnetic stimulus is applied to a patient in the state where the patient sits on the magnetic stimulator, and preferably, the tube of the pressure transducer is disposed under pelvic floor muscles of the patient who sits on the magnetic stimulator.

According to a second aspect of the invention, there is provided a control method for a biofeedback apparatus including a pressure transducer having a tube disposed under pelvic floor muscles of a patient and a controller, the control method including steps of: (a) measuring a pressure signal of the pressure transducer in the state where the patient does not constrict the pelvic floor muscles and setting the pressure signal as a reference pressure value; (b) measuring the pressure signal of the pressure transducer in the state where the patient constricts the pelvic floor muscles or does not constrict the pelvic floor muscles and obtains a value of difference between the measured pressure signal and the reference pressure value to generate a biofeedback signal; and (c) outputting the biofeedback signal.

According to a third aspect of the invention, there is provided a control method for a biofeedback apparatus including a pressure transducer having a tube disposed under pelvic floor muscles of a patient, a controller, and a magnetic stimulator, the control method including steps of: (a) measuring a pressure signal of the pressure transducer in the state where the patient does not constrict the pelvic floor muscles and setting the pressure signal as a reference pressure value; (b) measuring the pressure signal of the pressure transducer in the state where the patient constricts the pelvic floor muscles or does not constrict the pelvic floor muscles and obtains a value of difference between the measured pressure signal and the reference pressure value to generate a biofeedback signal; and (c) displaying the biofeedback signal; and (d) determining a strength of a magnetic field corresponding to the biofeedback signal, generating a stimulator driving signal for driving the magnetic stimulator according to the determined strength of the magnetic field, and supplying the stimulator driving signal to the magnetic stimulator to drive the magnetic stimulator.

In the above control method for the biofeedback apparatus according to the third aspect, preferably, the steps (c) and (d) are simultaneously performed, so that the biofeedback signal and the strength of the magnetic field are displayed together.

In the biofeedback apparatus according to the invention, a change in pressure is measured according to the movement of the pelvic floor muscles around vagina, urethra, or the like without insertion of a tool for measurement of a pressure or an EMG signal into the body cavity such as vagina or urethra, so that it is possible to measure the biofeedback signal for the urinary incontinence treatment.

In addition, in the biofeedback apparatus according to the invention, without insertion of a tool into the human body, the magnetic stimulation and the monitoring are configured to be simultaneously performed or the magnetic stimulation and the monitoring are cooperatively performed, so that it is possible to maximize the effect of treatment using the biofeedback.

In particular, in the case where the biofeedback apparatus according to the invention is used for the urinary incontinence treatment, without insertion of a tool for pressure measurement into the body cavity such as vagina or urethra, the change in pressure according to muscle exercise of vagina, urethra, or the like can be measured, and the pressure change measurement and the magnetic stimulation can be performed.

As a result, the change of the state of pressure according to the applied magnetic stimulus can be monitored in real time.

Therefore, in the biofeedback apparatus according to the invention, the patient can perform the pressure measurement and the magnetic stimulation in a comfortable condition, so that it is possible to maximize the effect of treatment of the urinary incontinence.

DETAILED DESCRIPTION OF THE PREFERRED EMBODIMENTS

Hereinafter, a biofeedback apparatus using a magnetic stimulator and a control method of a controller according to exemplary embodiments of the invention will be described with reference to the attached drawings. In the biofeedback apparatus according to the exemplary embodiment of the invention, a tube filled with a fluid is disposed between the magnetic stimulator and patient's pelvic floor muscles, a change in pressure according to exercise of the pelvic floor muscles is measured, and the measured change in pressure is monitored or treatment is performed by applying a magnetic stimulus, so that the effect of urinary incontinence treatment can be maximized. In particular, the biofeedback apparatus according to the invention can simultaneously perform monitoring and magnetic stimulator treatment, so that the effect of urinary incontinence treatment can be further improved.

Figure 1:
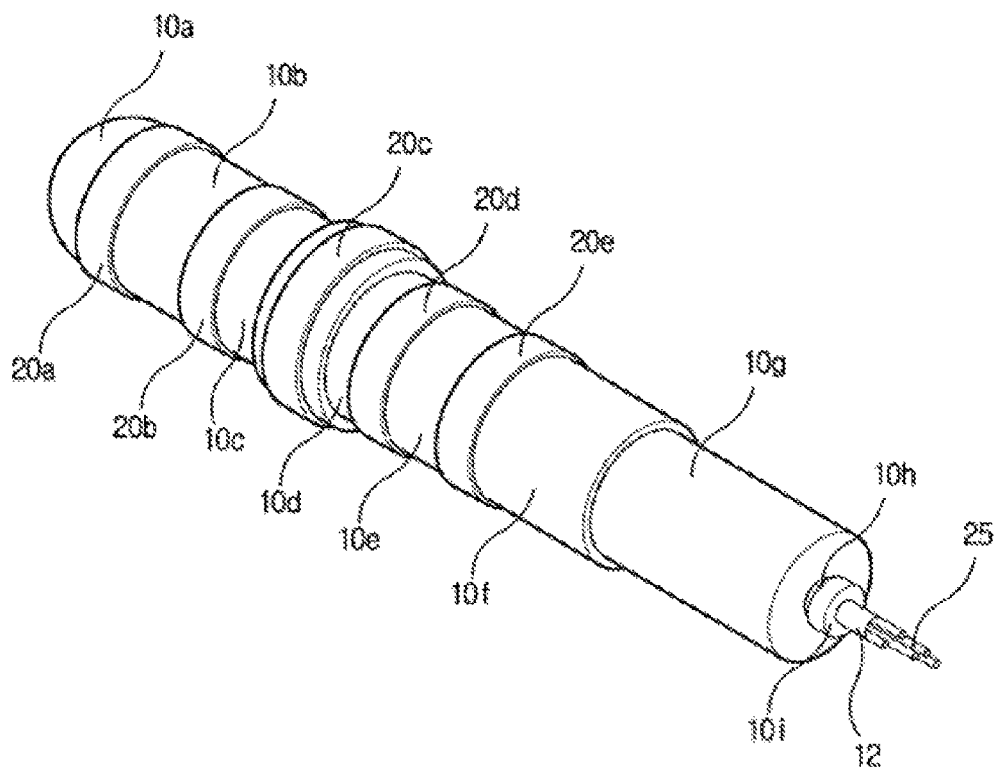
FIG. 1 is a perspective diagram illustrating a body-cavity insertion electrode used for an electric stimulator in the related art.
Figure 2:
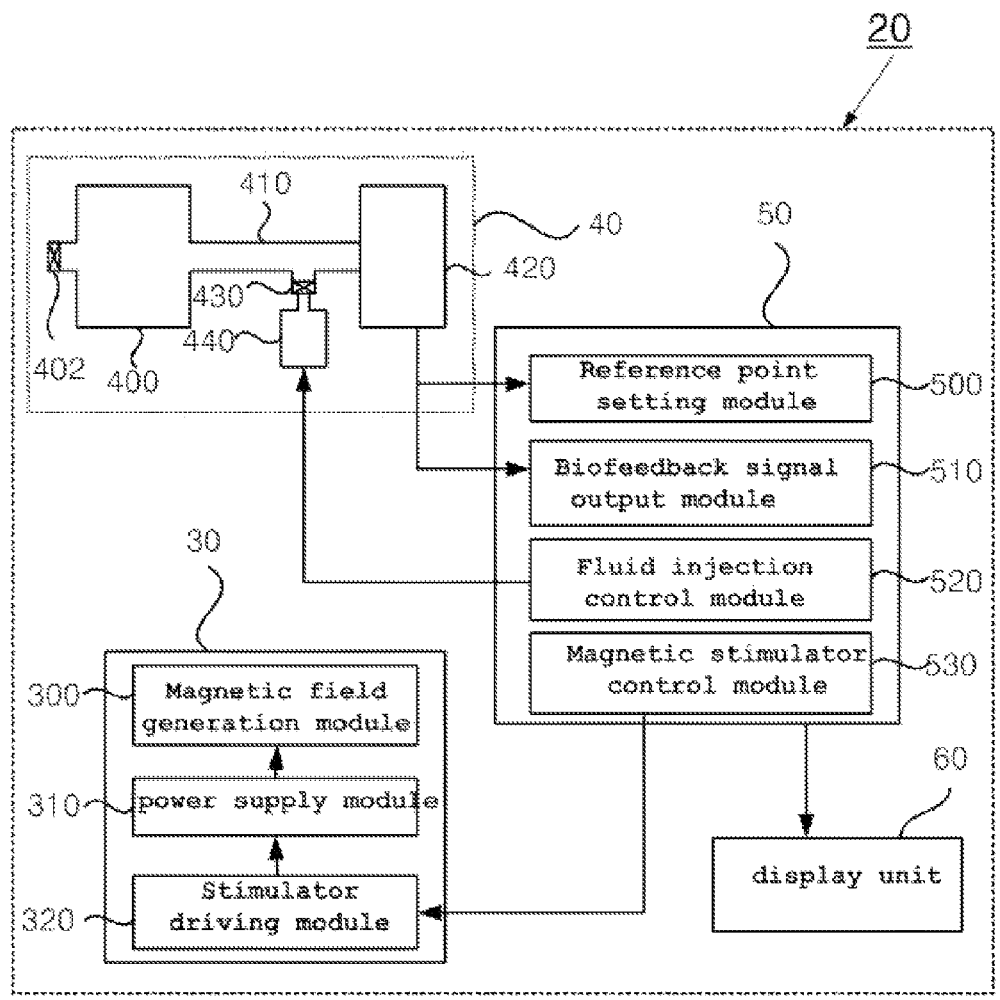
FIG. 2 is an overall configuration diagram illustrating a biofeedback apparatus 20 using a magnetic stimulator according to an exemplary embodiment of the invention.

FIG. 2 is an overall configuration diagram illustrating a biofeedback apparatus 20 using a magnetic stimulator according to the exemplary embodiment of the invention. Referring to FIG. 2, the biofeedback apparatus 20 includes a magnetic stimulator 30, a pressure transducer 40, a display unit 60, and a controller 50.

The magnetic stimulator 30 includes a magnetic field generation module 300, a power supply module 310 supplying power to the magnetic field generation module, and a stimulator driving module 320 controlling driving of the power supply module and the magnetic field generation module. The stimulator driving module controls the power supply module according to the stimulator driving signal supplied from the controller 50 to adjust voltage and current applied to the magnetic field generation module and, as a result, the stimulator driving module adjusts the strength of the magnetic field. The magnetic field generation module 300 is configured with a core and a coil winding around the core or is configured with only a coil without a core. The strength of the induced magnetic field is determined according to an intensity of power supplied from the power supply module to the coil.

In the case where the biofeedback apparatus according to the invention is used as a urinary incontinence treatment apparatus, preferably, the magnetic stimulator is installed in a housing having a shape of a chair which a patient sits on. A magnetic field is induced by the above-described magnetic stimulator, and treatment is performed by applying the magnetic stimulus to the muscles such as pelvic floor muscles of a patient who sits on a chair by using the magnetic field.

Unlike the electric stimulator, since the above-described magnetic stimulator is not inserted into the human body, the use is convenient, and the problem of the electric stimulator such as bacterial infection can be avoided.

The pressure transducer 40 senses a pressure applied from an outside by using a fluid and supplies a pressure signal to the controller 50. The pressure transducer includes a tube 400 having an air outlet 402, a pressure transfer member 410, a pressure sensor 420, a fluid inlet 430, and a fluid injector 440.

The tube 400 is configured with a soft material of which shape is variable according to an external pressure and is filled with the fluid. Preferably, the fluid which the inside of the tube is filled with is configured with a flowable material which is non-conductive or non-magnetic so as not to be influenced by a magnetic field or an electromagnetic field, so that even though the fluid is used together with the magnetic stimulator, the fluid is not influenced by the magnetic stimulator.

As an example of the fluid, a liquid such as distilled water or oil, flowable gel, or the like can be used.

The tube has the air outlet 402 so as to discharge air formed in an inner portion of the tube or the pressure transfer member.

The pressure sensor 420 senses a change in pressure of the tube through the pressure transfer member and converts the sensed pressure into an electrical pressure signal to output the pressure signal to the controller.

The pressure transfer member 410 is disposed between the tube and the pressure sensor to transfer a degree of the change in pressure of the tube to the pressure sensor.

In the embodiment of the invention, the pressure transfer member may be configured as a connection pipe which connects the tube and the pressure sensor. One end of the connection pipe is connected to the tube, and the other end of the connection pipe is in contact with the pressure sensor. The connection pipe is configured with a rigid material of which shape is not variable although an external pressure is applied. The inner portion of the connection pipe is connected to the tube to be filled with the same fluid as that of the tube. Therefore, due to the movement of the fluid, the pressure applied to the tube is transferred to the pressure sensor. Any structure capable of transferring the pressure of the tube to the pressure sensor can be used to the above-described pressure transfer member even though the structure is not disclosed in the specification. The structure of the pressure transfer member can be modified in various forms.

The fluid inlet 430 is formed in the tube to allow the fluid to be injected into the tube or to allow the fluid to be discharged to the outside. In the case where the pressure transfer member is configured with the connection pipe, the fluid inlet is selectively formed in a predetermined area of the tube or the connection pipe to allow the fluid to be injected into the tube or the connection pipe or to allow the fluid to be discharged. The fluid injector 440 is connected to the fluid inlet 430. The fluid injector is configured to be connected to the controller so that the fluid injector is automatically or manually driven.

The fluid injector is configured with a fluid tank having a shape of a cylinder capable of storing the fluid, a nozzle of the fluid tank connected to the fluid inlet, and a piston extruding or sucking the fluid of the fluid tank. Preferably, in order to realize the fluid injector to be automatically driven, a motor is connected to the piston of the fluid injector, so that the fluid injector can be automatically driven by using the motor. The fluid injector may be configured with various forms, and the fluid is not limited to the forms described in the specification.

Figure 3:
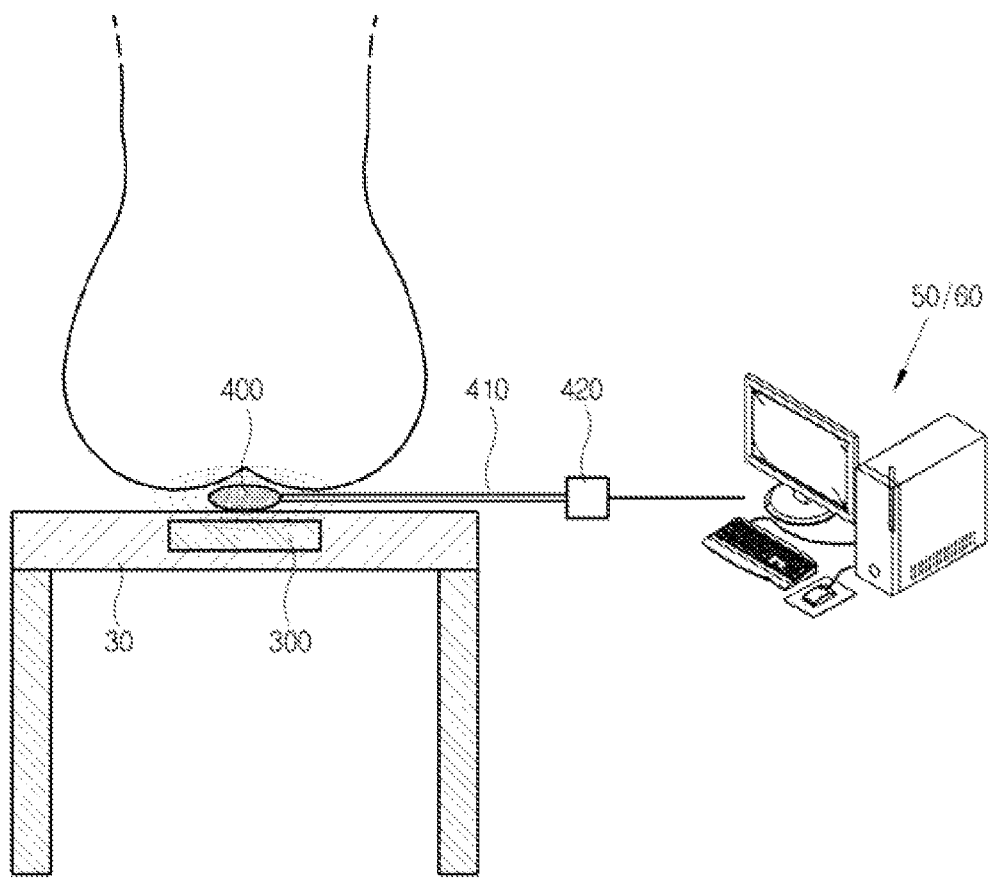
FIG. 3 is a cross-sectional diagram illustrating an exemplary use state of the biofeedback apparatus according to the exemplary embodiment of the invention.

FIG. 3 is a cross-sectional diagram illustrating an exemplary use state of the biofeedback apparatus according to the exemplary embodiment of the invention. Referring to FIG. 3, the tube 400 of the pressure transducer is mounted on the magnetic stimulator 30 having a shape of a chair, and in the state where a patient sits on the magnetic stimulator, the tube is disposed under the patient's pelvic floor muscles ('a'). When the patient does muscle exercise to constrict the pelvic floor muscles, a pressure is applied to the tube due to the movement of the pelvic floor muscles according to the muscle exercise. The pressure applied to the tube is transferred to the pressure sensor through the connection pipe, and the pressure sensor senses the pressure. In this manner, in the biofeedback apparatus according to the invention, the change in muscle strength of vagina, urethra, or the like can be measured by measuring the change in pressure according to the movement of the pelvic floor muscles without insertion of a tool into a human body such as vagina or urethra.

The display unit 60 is an image output device which outputs an image signal supplied from the controller on the screen.

The controller 50 generates a biofeedback signal by using the pressure signal supplied from the pressure transducer to output the biofeedback signal to the display unit or control driving of the magnetic stimulator. The controller 50 includes a reference point setting module 500, a biofeedback signal output module 510, a fluid injection control module 520, and a magnetic stimulator control module 530.

The reference point setting module 500 receives the pressure signal from the pressure transducer and sets the reference pressure value by using the pressure signal according to a reference pressure value setting request input by the user. In the case where the biofeedback apparatus according to the invention is used as a urinary incontinence treatment apparatus, the tube of the pressure transducer is disposed under patient's pelvic floor muscles, and after that, in the state where the patient does not constrict the pelvic floor muscles, the pressure signal is measured multiple times, and the average value thereof is set as the reference pressure value.

In another example of the reference point setting module of the control according to the invention, the reference pressure value is set in advance, and in the state where the patient does not constrict the pelvic floor muscles, the internal pressure of the tube is adjusted by injecting the fluid into the tube or discharging the fluid so that the value of the pressure in the state where the patient does not constrict the pelvic floor muscles reaches the aforementioned reference pressure value.

Figure 4:
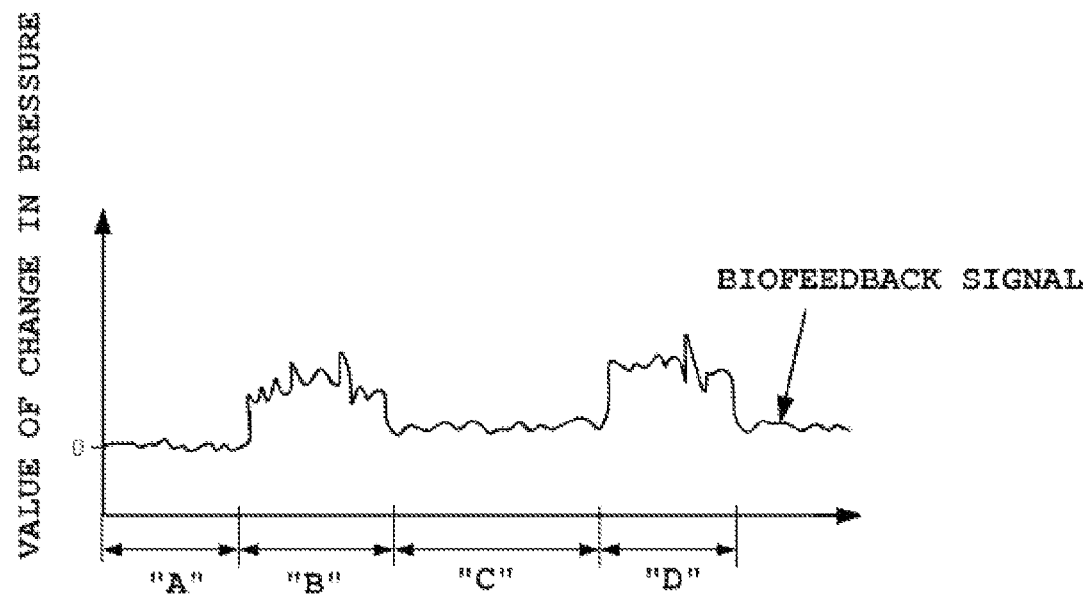
FIG. 4 is an exemplary graph illustrating a biofeedback signal output to a display unit in the biofeedback apparatus according to the exemplary embodiment of the invention.

The biofeedback signal output module 510 receives the pressure signal from the pressure transducer and detects a value of difference between the received pressure signal and the reference pressure value, that is, a degree of change in pressure signal with respect to the reference pressure value to output the value of difference as a biofeedback signal. The biofeedback signal is output to the display unit. FIG. 4 illustrates an exemplary graph of the biofeedback signal output to the display unit in the biofeedback apparatus according to the exemplary embodiment of the invention.

FIG. 4 illustrates the change in pressure between the state where the patient constricts the pelvic floor muscles and the state where the patient releases the pelvic floor muscles according to the muscle exercise. In FIG. 4, sections "A" and "C" illustrate the value of change in pressure of the pelvic floor muscles in the state where the patient does not constrict the muscles, and sections "B" and "D" illustrate the value of change in pressure of the pelvic floor muscles in the state where the patient constricts the muscles.

Since the pressure transducer of the biofeedback apparatus according to the invention is not inserted into vagina, urethra, or the like, the value of pressure of the vagina, urethra, or the like is difficult to accurately measure. However, it is possible to accurately measure the change in pressure according to the muscle exercise of the vagina, urethra, or the like. The biofeedback apparatus according to the invention generates a biofeedback signal by using the measured change in pressure.

In the case where the pressure signal supplied from the pressure transducer deviates from a pre-defined allowable range, the fluid injection control module 520 determines a fluid amount to be injected into the tube or discharged from the tube according to a degree of deviation from the allowable range and generates a fluid injection driving signal according to a value of difference between the determined fluid amount and a current fluid amount of the tube to supply the fluid injection driving signal to the fluid injector. The fluid injector injects the fluid into the tube or discharges the fluid according to the fluid injection driving signal supplied from the fluid injection control module.

The magnetic stimulator control module 530 receives the biofeedback signal from the biofeedback signal output module, determines the strength of the magnetic field corresponding to the biofeedback signal, generates a stimulator driving signal for driving the magnetic stimulator according to the determined strength of magnetic field, and supplies the stimulator driving signal to the magnetic stimulator. The magnetic stimulator control module separately controls the outputting of the biofeedback signal and the driving of the magnetic stimulator. However, according to user's selection, the magnetic stimulator control module may simultaneously control the outputting of the biofeedback signal and the driving of the magnetic stimulator.

Preferably, the magnetic stimulator control module outputs the biofeedback signal and the determined strength of magnetic field to the screen of the display unit.

Therefore, in the biofeedback apparatus according to the invention, the biofeedback signal output module can output the biofeedback signal to the display unit, and at the same time, the magnetic stimulator control module can drive the magnetic stimulator according to the strength of the magnetic field corresponding to the biofeedback signal.

In this manner, in the biofeedback apparatus according to the invention, since the driving of the magnetic stimulator and the driving of the pressure transducer do not influence each other, the controller can continuously monitor the state of change in pressure of the pelvic floor muscles by using the pressure transducer and, at the same time, can adjust the strength of the magnetic field generated from the magnetic stimulator to an optimal strength according to the monitored state, so that it is possible to maximize the effect of treatment.

On the other hand, in the biofeedback apparatus according to the invention, according to user's selection, the outputting of the biofeedback signal and the driving of the magnetic stimulator may be separately performed.

Figure 5:
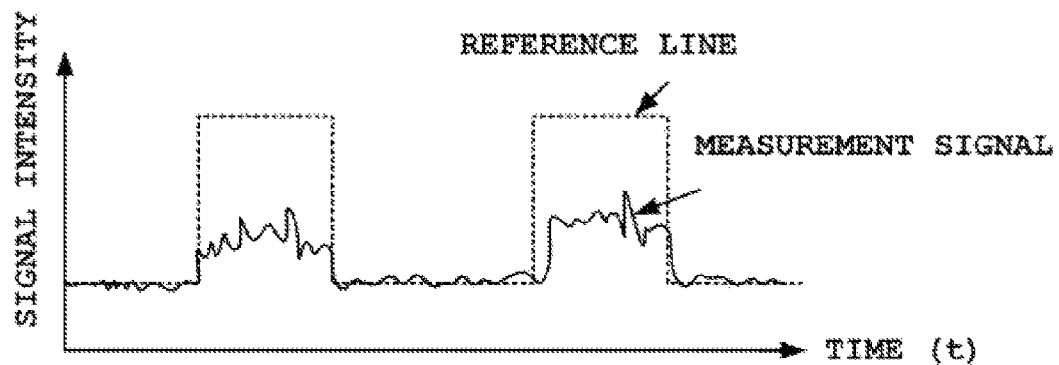
FIG. 5 is an exemplary graph illustrating an EMG (electromyogram) measurement signal in a body cavity which is measured and supplied by using a biofeedback apparatus in the related art.

FIGS. 5 and 6 are exemplary graphs illustrating signals measured by the biofeedback apparatus of the related art and the biofeedback apparatus according to the invention in order to compare the effects of the biofeedback apparatuses.

FIG. 5 is an exemplary graph illustrating an EMG measurement signal in a body cavity measured and supplied by the biofeedback apparatus of the related art. In FIG. 5, a reference line indicates starting and ending time points of the section when the patient constricts the muscles and a required strength of constriction force. On the other hand, when the patient starts constricting the muscles according to the reference line, the biofeedback apparatus measures the EMG signal in the body cavity such as vagina or urethra and displays the EMG signal on the graph to perform monitoring and biofeedback. However, the biofeedback apparatus of the related art illustrated in FIG. 5 cannot apply an electric stimulus during the section when the patient constricts the muscles.

Figure 6A:
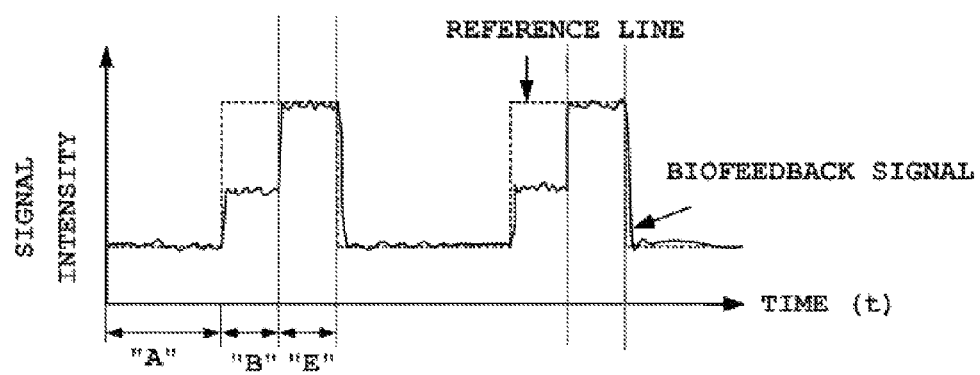
FIG. 6A is a graph illustrating a biofeedback signal obtained by using a pressure signal measured by a pressure transducer in the biofeedback apparatus according to the invention.
Figure 6B:
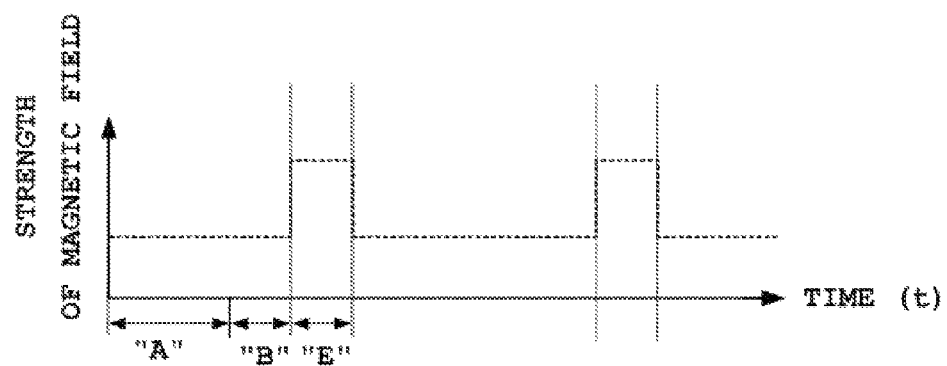
FIG. 6B is a graph illustrating a strength of a magnetic field generated in the magnetic stimulator according to the biofeedback signal.

FIG. 6A is a graph illustrating information on the pressure measured by the pressure transducer in the biofeedback apparatus according to the invention, and FIG. 6B is a graph illustrating the strength of the magnetic field generated by the magnetic stimulator according to the pressure. In FIG. 6A, section "A" indicates a reference pressure value, that is, pressure by the pelvic floor muscles measured in the state where the patient does not constricts the pelvic floor muscles, section "B" indicates pressure in the case where the patient constricts the pelvic floor muscles according to the reference line, and section "E" indicates pressure in the case where the patient constricts the pelvic floor muscles and, at the same time, the magnetic stimulus is applied. FIG. 6B illustrates the strength of the magnetic stimulus applied in the section "E".

As illustrated in FIGS. 6A and 6B, in the biofeedback apparatus according to the invention, it is possible to simultaneously perform the treatment using the magnetic stimulus and the monitoring by the pressure measurement. As a result, in the case where the strength of the magnetic field does not reach a reference force, while monitoring the patient's own state in real time, the patient adjusts the strength of the magnetic field of the magnetic stimulator to reach the reference force, so that the magnetic stimulation treatment can be performed. Therefore, it is possible to further improve the effect of the biofeedback apparatus.

An apparatus according to the invention can be widely used in the medical field for urinary incontinence treatment or the like.

While the present invention has been particularly shown and described with reference to exemplary embodiments thereof, it will be understood by those skilled in the art that various changes in form and details may be made therein without departing from the spirit and scope of the present invention as defined by the appended claims.

What is claimed is:
1. A biofeedback apparatus comprising:
 a pressure transducer which senses a pressure applied from an outside of the pressure transducer by using a fluid and supplies a pressure signal;
 a controller which generates a biofeedback signal by using the pressure signal supplied from the pressure transducer and outputs the biofeedback signal;
 a display unit which outputs the biofeedback signal supplied from the controller on a screen;
 a magnetic stimulator which generates and emits a magnetic field according to a stimulator driving signal; and
 a magnetic stimulator control module which receives the biofeedback signal from the controller, determines a strength of the magnetic field corresponding to the biofeedback signal, and generates the stimulator driving signal for driving the magnetic stimulator according to the determined strength of the magnetic field to supply the stimulator driving signal to the magnetic stimulator, wherein the pressure transducer includes:
a tube which is configured with a soft material of which shape is variable according to an external pressure and is filled with the fluid;
a pressure sensor which senses the pressure applied to the tube to output a pressure signal; and
a pressure transfer member which is disposed between the tube and the pressure sensor to transfer the pressure of the tube to the pressure sensor, and
wherein the tube of the pressure transducer is disposed at a position which is influenced by the magnetic field of the magnetic stimulator, and the pressure sensor is disposed at a position which is not influenced by the magnetic field of the magnetic stimulator.

2. The biofeedback apparatus according to claim 1, wherein the fluid is configured with a flowable material which is non-conductive and non-magnetic so as not to be influenced by a magnetic field or an electromagnetic field.

3. The biofeedback apparatus according to claim 1, wherein the controller includes a biofeedback signal output module which receives the pressure signal from the pressure transducer, detects a value of difference between the received pressure signal and a pre-defined reference pressure value, and outputs the value of difference as the biofeedback signal.

4. The biofeedback apparatus according to claim 1, wherein the controller includes a reference point setting module which receives the pressure signal from the pressure transducer and sets a reference pressure value by using the received pressure signal according to a reference pressure value setting request input from an outside.

5. The biofeedback apparatus according to claim 1, wherein the controller includes a reference point setting module which injects the fluid into the tube of the pressure transducer or discharges the fluid from the tube so that an internal pressure of the tube reaches a pre-defined reference pressure value according to a reference pressure value setting request input from an outside.

6. The biofeedback apparatus according to claim 1, wherein the pressure transfer member is configured with a connection pipe which connects the tube and the pressure sensor, an inner portion of the connection pipe is connected to the tube to be filled with a same fluid as that of the tube, and due to movement of the fluid, the pressure applied to the tube is transferred to the pressure sensor.

7. The biofeedback apparatus according to claim 1, wherein the pressure transducer further includes a fluid inlet which is formed in the tube, and an internal pressure of the tube is adjusted by further injecting or discharging the fluid through the fluid inlet.

8. The biofeedback apparatus according to claim 7, wherein the tube further includes an air outlet, and air of an inner portion of the tube is discharged to an outside of the tube through the air outlet.

9. The biofeedback apparatus according to claim 7, wherein the pressure transducer further includes a fluid injector connected to the fluid inlet, and
wherein the fluid injector injects the fluid into the tube or discharges the fluid from the tube through the fluid inlet.

10. The biofeedback apparatus according to claim 9, wherein the fluid injector is configured so as to automatically inject the fluid according to a fluid injection driving signal supplied from the controller,
wherein the controller further includes a fluid injection control module, and wherein, in the case where the pressure signal supplied from the pressure transducer deviates from a pre-defined allowable range, the fluid injection control module determines a fluid amount to be injected into the tube or discharged from the tube according to a degree of deviation from the allowable range and generates a fluid injection driving signal according to a value of difference between the determined fluid amount and a current fluid amount to supply the fluid injection driving signal to the fluid injector.

11. The biofeedback apparatus according to claim 1, wherein the magnetic stimulator control module outputs the biofeedback signal supplied from the pressure transducer and the determined strength of the magnetic field to the display unit.

12. The biofeedback apparatus according to claim 1, wherein the magnetic stimulator control module outputs the biofeedback signal supplied from the controller to the display unit and, at the same time, determines the strength of the magnetic field corresponding to the biofeedback signal and generates the stimulator driving signal for driving the magnetic stimulator according to the determined strength of the magnetic field to supply the stimulator driving signal to the magnetic stimulator.

13. The biofeedback apparatus according to claim 1,
wherein the biofeedback apparatus is used for urinary incontinence treatment, and
wherein the tube is disposed under pelvic floor muscles of a patient.

14. The biofeedback apparatus according to claim 1,
wherein the biofeedback apparatus is used for urinary incontinence treatment,
wherein the magnetic stimulator is formed to have a shape of a chair so that a magnetic stimulus is applied to a patient in a state where the patient sits on the magnetic stimulator, and
wherein the tube of the pressure transducer is disposed under pelvic floor muscles of the patient who sits on the magnetic stimulator.

15. A biofeedback apparatus comprising:
a pressure transducer which senses a pressure applied from an outside of the pressure transducer by using a fluid and supplies a pressure signal;
a controller which generates a biofeedback signal by using the pressure signal supplied from the pressure transducer and outputs the biofeedback signal; and
a display unit which outputs the biofeedback signal supplied from the controller on a screen,
wherein the pressure transducer includes:
a tube which is configured with a soft material of which shape is variable according to an external pressure and is filled with the fluid;
a pressure sensor which senses the pressure applied to the tube to output a pressure signal; and
a pressure transfer member which is disposed between the tube and the pressure sensor to transfer the pressure of the tube to the pressure sensor, and
wherein the controller includes a reference point setting module which receives the pressure signal from the pressure transducer and sets a reference pressure value by using the received pressure signal according to a reference pressure value setting request input from an outside.

16. A biofeedback apparatus comprising:
a pressure transducer which senses a pressure applied from an outside of the pressure transducer by using a fluid and supplies a pressure signal;

a controller which generates a biofeedback signal by using the pressure signal supplied from the pressure transducer and outputs the biofeedback signal; and a display unit which outputs the biofeedback signal supplied from the controller on a screen, wherein the pressure transducer includes:

a tube which is configured with a soft material of which shape is variable according to an external pressure and is filled with the fluid;

a pressure sensor which senses the pressure applied to the tube to output a pressure signal; and a pressure transfer member which is disposed between the tube and the pressure sensor to transfer the pressure of the tube to the pressure sensor, wherein the controller includes a reference point setting module which injects the fluid into the tube of the pressure transducer or discharges the fluid from the tube so that an internal pressure of the tube reaches a pre-defined reference pressure value according to a reference pressure value setting request input from an outside.

* * * * *